(12) United States Patent
Finkelman

(10) Patent No.: US 9,763,755 B2
(45) Date of Patent: Sep. 19, 2017

(54) SURGICAL KIT FOR PRECISE VERTICAL POSITIONING OF DENTAL IMPLANTS

(71) Applicant: Abraham Finkelman, Hertzelia (IL)

(72) Inventor: Abraham Finkelman, Hertzelia (IL)

( * ) Notice: Subject to any disclaimer, the term of this patent is extended or adjusted under 35 U.S.C. 154(b) by 0 days.

(21) Appl. No.: 14/620,215

(22) Filed: Feb. 12, 2015

(65) Prior Publication Data

US 2016/0278888 A1    Sep. 29, 2016

(51) Int. Cl.
| | |
|---|---|
| *A61C 8/00* | (2006.01) |
| *A61C 1/08* | (2006.01) |
| *A61C 19/02* | (2006.01) |
| *A61C 19/04* | (2006.01) |
| *A61B 90/00* | (2016.01) |

(52) U.S. Cl.
CPC ............ *A61C 8/0089* (2013.01); *A61C 1/084* (2013.01); *A61C 19/02* (2013.01); *A61C 19/04* (2013.01); *A61B 2090/062* (2016.02)

(58) Field of Classification Search
CPC .. A61C 8/0089; A61C 1/084; A61B 2090/062
USPC ..................................................... 433/75, 76
See application file for complete search history.

(56) References Cited

U.S. PATENT DOCUMENTS

| | | | | |
|---|---|---|---|---|
| 5,118,294 A | * | 6/1992 | Kurer ..................... | A61C 13/30 433/174 |
| 5,556,278 A | * | 9/1996 | Meitner ................. | A61C 1/084 433/213 |
| 5,613,852 A | * | 3/1997 | Bavitz .................... | A61C 1/084 433/173 |
| 5,967,777 A | * | 10/1999 | Klein ..................... | A61C 1/084 433/75 |
| 2010/0151412 A1 | * | 6/2010 | Suter .................... | A61C 8/0089 433/75 |
| 2010/0311006 A1 | * | 12/2010 | Lancieux ............... | A61C 1/084 433/75 |

* cited by examiner

*Primary Examiner* — Pedro Philogene
*Assistant Examiner* — David C Comstock
(74) *Attorney, Agent, or Firm* — Knobbe, Martens, Olson & Bear LLP

(57) ABSTRACT

The present invention relates to dental cylindered pins suitable for controlling the amount of jaw-bone to be removed prior to placement of a dental implant into a drilled implant socket, for enabling easy and simple positioning of a dental implant, as well as to kits comprising said pins, and method of use.

12 Claims, 4 Drawing Sheets

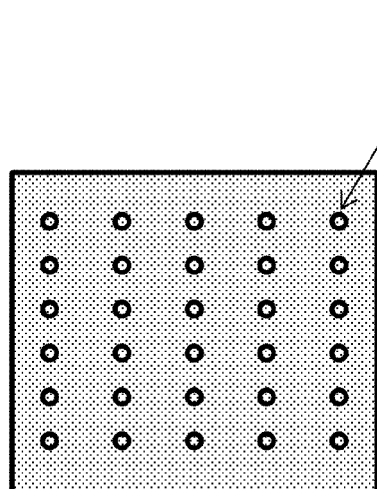
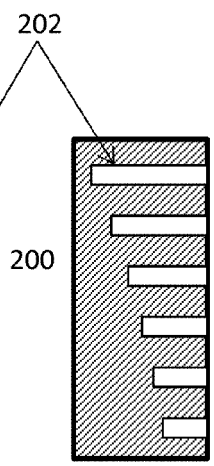
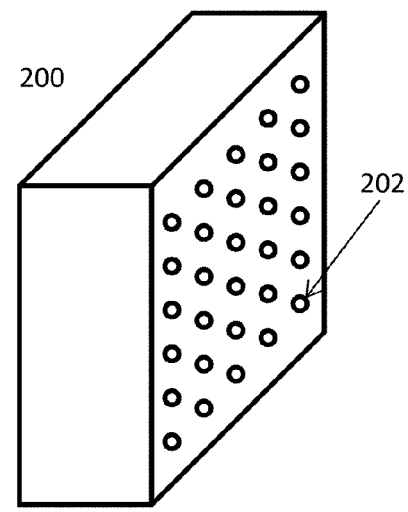
Figure 2A  Figure 2B  Figure 2C
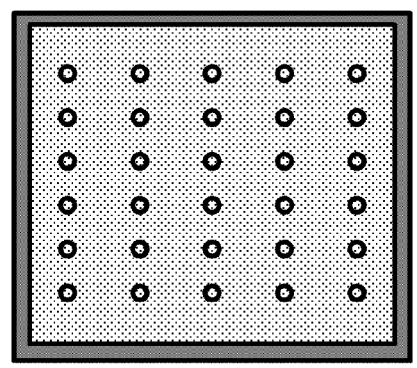
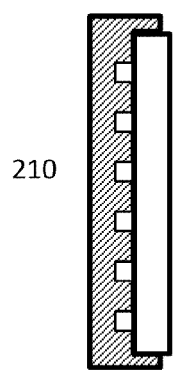
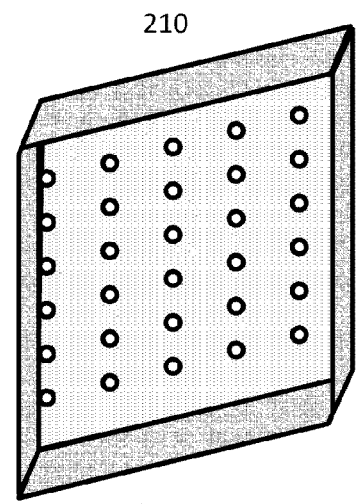
Figure 2D  Figure 2E  Figure 2F

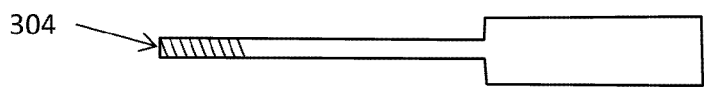
Figure 4A
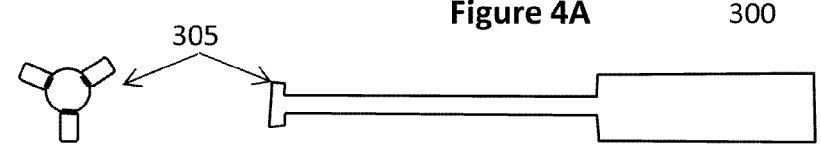
Figure 4C
Figure 4B
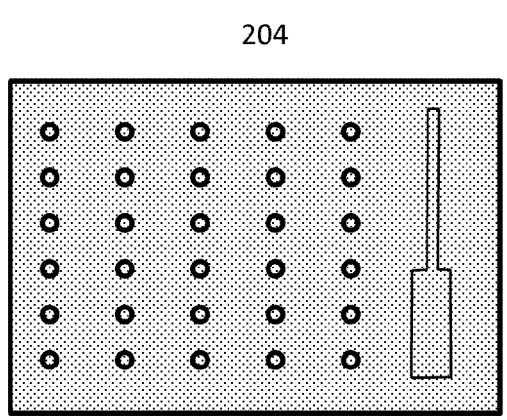
Figure 4D
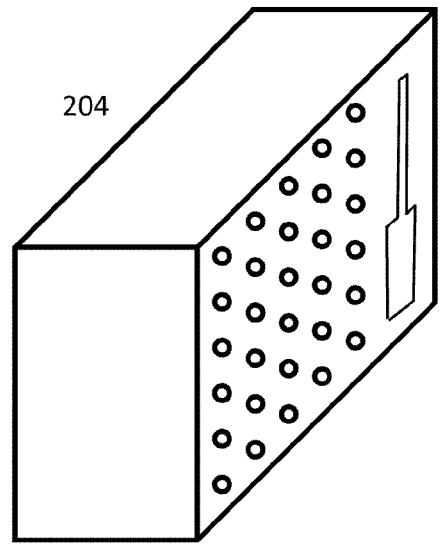
Figure 4E

SURGICAL KIT FOR PRECISE VERTICAL POSITIONING OF DENTAL IMPLANTS

FIELD OF THE INVENTION

The present invention relates to a device, more particularly a dental cylindered pin, for enabling easy and simple positioning of a dental implant, kit comprising said device, and method of use.

BACKGROUND OF THE INVENTION

Dental implants have become popular in recent years as a way to provide permanent artificial teeth to patients that lost some or all of their teeth. Implant dentistry involves the restoration of one or more teeth in a patient's mouth using artificial components, such as dental implants and a prosthetic tooth and/or an abutment that is secured to the dental implant: the dentist drills into the patient's jaw bone and implants an artificial tooth root, i.e., a dental implant. Then, natural bone, by a process called osseointegration, fuses with this implant. An artificial crown can then be placed onto the implant.

Due to the hazards of improper drilling, computerized surgical guides have become a reliable method for performing implant surgery. This guides use computerized tomography and three-dimensional (3D) materials fabrication technology (e.g., computer controlled steriolithography, computer numerical control (CNC) machining, and the like) to create a custom implant drilling guide. This way, the guide provides control of the buco-lingual, mesial-distal and vertical placement of the surgical drills. Following the drilling process, there is often a need to further remove bone excess around the implant socket. This bone removal can be done by manually removing the bone excess after drilling according to rough estimation; creating another computerized reduction guide prior to the implant drilling guide; or removing the bone excess after screwing the implant into place.

However, each way has its disadvantages. For instance, manually removing the bone excess after drilling according to rough estimation is highly risky, due to the risk of excessive, undesired bone removal; creating another computerized reduction guide prior to the implant drilling guide requires the production of an additional computerized surgical guide just for the bone removal step, which dramatically increases the cost of the treatment and prolongs the overall duration of the procedure (i.e., by removing the first guide and placing the second one); and removing the bone excess after screwing the implant into place, particularly in the surrounding of the implant, might damage the neck surface of the implant.

Therefore, there is an unmet need for developing new, simple and cost efficient ways for removal of excess jawbone around an implant socket.

SUMMARY OF INVENTION

In one aspect, the present invention provides a dental cylindered pin 100 suitable for controlling the amount, i.e., the amount and level, of jaw-bone to be removed prior to placement of a dental implant into a drilled implant socket, said dental cylindered pin 100 having an outer diameter in a range of about 2.0 mm to about 4.5 mm and a length in a range of about 3.5 to about 18 mm.

In another aspect, the present invention provides a dental kit comprising: (i) at least one dental cylindered pin 100, each independently as defined above; and (ii) an insertion/removal apparatus 300 for inserting/removing said at least one dental cylindered pin 100 into/from an implant socket. The kit of the present invention may further comprise a container having a body 200,201 and a lid 210,211, designated for holding said at least one dental cylindered pin 100 and optionally said insertion/removal apparatus 300. Such a container 200,201 may be designed in various configurations, e.g., may comprise cavities 202,203 suited for holding said at least one dental cylindered pin 100 and optionally said insertion/removal apparatus 300 (FIGS. 4D and 4E).

In a further aspect, the present invention relates to a method for the safe removal of excess jaw-bone around a drilled implant socket, thereby adapting the depth of said implant socket to the length of a dental implant without the risk of excess removal of jaw-bone or damaging said dental implant. More particularly, the method of the present invention comprises the steps of: (i) selecting a dental cylindered pin 100 as defined above according to the diameter of the drilled implant socket and the length of the dental implant for insertion into said implant socket, wherein the length of said dental cylindered pin 100 is identical to the length of the dental implant; (ii) optionally attaching the selected dental cylindered pin 100 to an insertion/removal apparatus 300; (iii) placing said dental cylindered pin 100 in the drilled implant socket; (iv) performing excess jaw-bone removal around and up to the upper surface of said dental cylindered pin 100, thereby adapting the depth of the drilled implant socket to the length of the dental implant; (v) attaching said insertion/removal apparatus 300 to the dental cylindered pin 100; and (vi) removing the dental cylindered pin 100 from the depth-adapted implant socket.

BRIEF DESCRIPTION OF DRAWINGS

FIGS. 1A, 1C, 1E and 1G are upper view of each pin configuration, and FIGS. 1B, 1D, 1F and 1H are side-cross section thereof.

FIGS. 2A-2F show one configuration of the body 200 and lid 210 of the container of the invention.

FIGS. 4A-E show two possible configurations of an insertion/removal apparatus 300 (4A and 4B) and an example of one possible configuration of the tip of said apparatus (4C), along with a dedicated body 204 of the container of the invention with special cavity for said insertion/removal apparatus 300.

DETAILED DESCRIPTION OF THE INVENTION

Figure 1A:
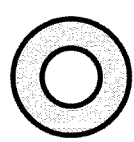
FIGS. 1A-1H show different configurations of the dental cylindered pin 100 of the invention.

The present invention provides a simple and safe way for removing excess jaw bone at a dental implant socket without the risk of damaging the dental implant or excessive and undesired bone removal. More particularly, the present invention provides means for assisting in performing the removal of excess jaw-bone around a dental implant prior the placement of the implant in its drilled socket, while maintaining a precise control of the vertical position of the implant as originally planned without damaging the implant surface. Specifically, the invention provides a dental pin 100 as defined above, i.e., a dental cylindered pin for controlling the amount of jaw-bone to be removed prior to placement of a dental implant into a drilled implant socket, wherein said dental cylindered pin 100 has an outer diameter of about 2.0 mm to about 4.5 mm and a length of about 3.5 mm to about 18 mm.

The dental cylindered pins 100 of the present invention may have various lengths and diameters, depending on the implant system being used. For instance, the dental cylindered pin 100 of the invention would have an external diameter that is smaller than that of the final drill being used, e.g., about 0.10, 0.15, 0.20, 0.25 mm, or more, smaller than the diameter of said final drill, for smooth insertion of said pin 100 into the drilled dental socket, and length that is identical to that of the dental implant to be used. For example, when the diameter of the final drill is 3.2 mm, the chosen dental cylindered pin 100 will have a diameter that is smaller than 3.2 mm, e.g., of about 3 mm.

In certain embodiments, the dental cylindered pin 100 of the invention has an external diameter in a range of about 2.0 mm to about 4.5 mm. In particular embodiments, the external diameter of the dental cylindered pin 100 of the invention is about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5 mm. It should be understood that the diameter of the dental pin 100 may also be smaller or bigger, depending on the final drill being used when preparing the dental implant socket, and preferably at least about 0.1, 0.15 or 0.2 smaller that the diameter of said final drill. More particularly, such dental cylindered pins 100 have an external diameter of about 2.6, 3.0, 3.6, or 4.2 mm.

In certain embodiments, the dental cylindered pin 100 of the invention has a length that is identical to that of the dental implant being used, i.e., any length in the range of about 3.5 mm to about 18 mm. For instance, the length of the dental cylindered pin may be about 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25, 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.5, 16.75, 17.0, 17.25, 17.5, 17.75 or 18.0 mm. It should be understood that the length of the dental pin may also be longer or shorter, depending on the length of the dental implant being used.

The dental cylindered pin 100 of the invention may be made of any suitable material, more particularly any suitable rigid material which enables easy insertion of the pin into a dental implant socket, and is preferably made of a medical graded material. The term "medical graded material" as used herein refers to any biocompatible rigid material which can be cleaned and sanitized by any suitable procedure/technique, and is preferably durable to jaw-bone drilling thus would not be easily damaged during bone site preparation, i.e., while removing excess jaw-bone around the dental implant socket prior to implantation. In certain embodiments, the dental cylindered pin 100 of the invention is made of a stainless steel, e.g., stainless steel 304, 304L, 316 or 316L. In other embodiments, the dental cylindered pin 100 of the invention is made of titanium or a titanium alloy, preferably those that are biocompatible such as Ti-6Al-7Nb and nickel-titanium (nitinol). In other embodiments, the dental cylindered pin 100 of the invention is made of any suitable carbon composite, or other suitable composites such as amalgam After sterilization, the dental cylindered pin of the invention can be contained in sealed packaging until use.

The dental cylindered pin 100 of the invention may be either hollow, or solid, i.e., not a hollow cylinder.

Figure 1B:
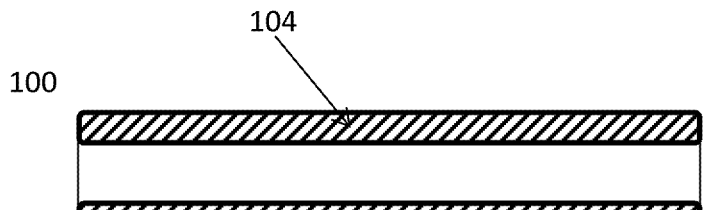
Figure 1C:
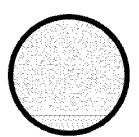
Figure 1D:
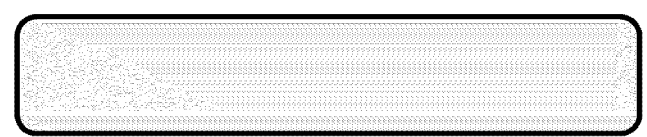
Figure 1E:
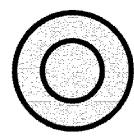
Figure 1F:
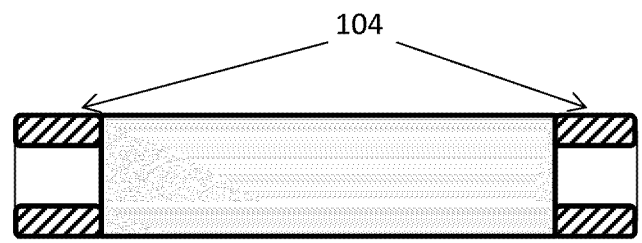

In certain embodiments, the dental cylindered pin 100 of the invention is a hollow cylinder (FIGS. 1A and 1B). Such a dental cylinder pin 100 may have in its interior wall a tapping tapped or a screw-like engraving 104 for enabling the easy attachment and release of an insertion/removal apparatus 300 designed for insertion/removal of the dental cylindered pin 100 into/from an implant socket by attaching-to and detaching-from said dental cylindered pin 100. In particular, hollow dental cylindered pins 100 having a screw-like engraving 104 in the interior wall, said screw-like engraving may either be engraved through the entire inner side (FIG. 1B) or only near both edges of the pin (FIG. 1F). It should be understood that hollow dental cylindered pins 100 (no matter whether having a tapping tapped or a screw-like engraving in the interior wall) having different external diameters may still, and preferably, have an identical internal diameter so as to match, i.e., be compatible with, a particular insertion/removal apparatus 300.

In alternative configurations, the dental cylindered pin 100 may have at one or both of its planes a special groove 105 (FIGS. 1G and 1H) designed for enabling the attachment of a special insertion/removal apparatus 300 (FIGS. 4B and 4C); or is completely solid (FIGS. 1C and 1D), wherein the insertion/removal apparatus 300 may use vacuum or magnetic force for attaching to the pin.

In certain embodiments, the dental cylindered pin 100 of the invention has a lifting groove 105 at one or both of its ends. The term "lifting groove" as used herein refers to any structure or configuration, such as a cavity, rail, channel, recess, ledge or depression, or an area surrounded by protruding ridges, which enables the insertion of adjusted protrusions 305 at the tip of the insertion/removal apparatus 300 and interlocking therebetween (FIGS. 4B and 4C). A lifting groove as referred to herein may alternatively be located at the tip of the insertion/removal apparatus, whereas the adjusted protrusions are located at one or both of the pin's planes/ends.

In another aspect, the present invention provides a dental kit comprising: (i) at least one dental cylindered pin 100, each independently as defined herein; and (ii) an insertion/removal apparatus 300 for inserting/removing said at least one dental cylindered pin 100 into/from an implant socket.

In certain embodiments, for the sake of order and ease of use, various dental cylindered pins 100 of either identical or different lengths and/or diameters are stored in a special container 200,201, separated according to their length and/or diameter. Optionally, a separate container is used for storing dental cylindered pins of identical diameters and different lengths. Alternatively, the container 200,201 may hold any number of dental cylindered pins 100 of any diameter and length.

Accordingly, in certain embodiments, the dental kit of the present invention further comprises a designated container having a body 200,201 and a lid 210,211, for holding said at least one dental cylindered pin 100 and optionally said insertion/removal apparatus 300 (FIGS. 4D and 4E). The container 200,201 holding said at least one dental cylindered pin 100 and optionally said insertion/removal apparatus 300 may be made of any suitable material, but it is preferably made of a material that is suitable for medical use and can be sterilized using a standard sterilization method. Particular such containers are made of medical graded materials such as, without being limited to, stainless steel, titanium, titanium alloys, plastic, and polycarbonates.

Figure 3A:
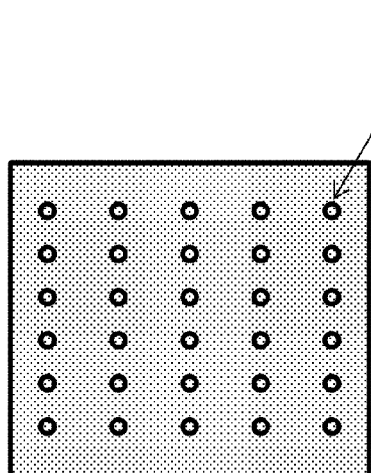
FIGS. 3A-3F show another configuration of the body 201 and lid 211 of the container of the invention.
Figure 3B:
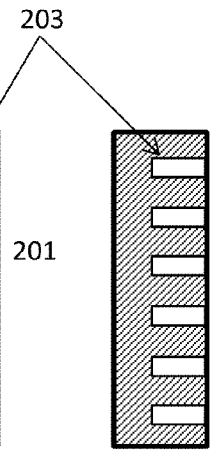
Figure 3C:
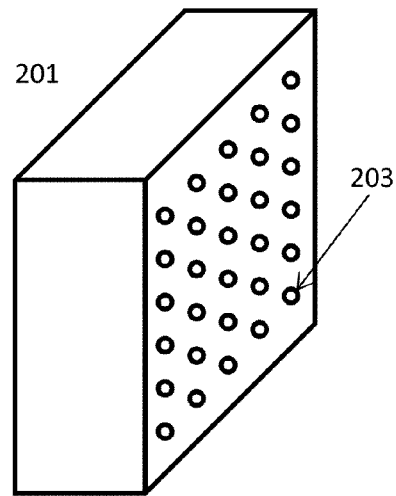
Figure 3D:
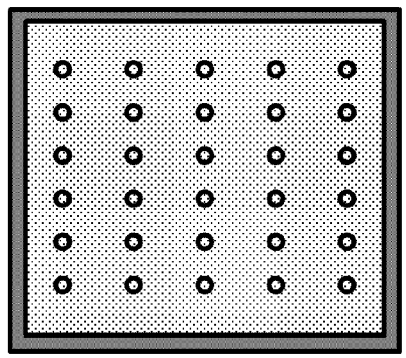
Figure 3E:
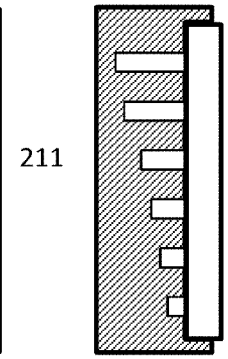
Figure 3F:
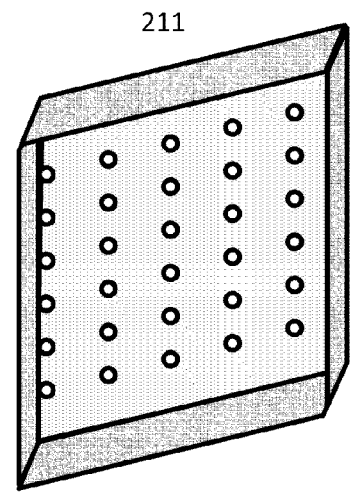

In certain embodiments, such designated container 200, 201 comprises cavities 202,203 suited for holding said at least one dental cylindered pin 100 and optionally said insertion/removal apparatus 300. For instance, such a container 200,201 may comprise 6 rows of 6 cavities, wherein each row is designed to hold 6 separate identical dental cylindered pins, and the difference between the rows is the length of the pins therein. In certain embodiments, the depth of each cavity 202 in said container 200 is constructed to align the upper surface of all the pins therein (FIGS. 2A-2C). Alternatively, all the cavities 203 in the container 201 have the same depth so that the pins 100 therein protrude according to their length (FIGS. 3A-3C). In such a case, the container's lid 211 is designed accordingly (FIGS. 3D-3F).

In certain embodiments, each dental pin 100 of the invention is engraved with its diameter and/or length, or with a marking indicating its diameter and length. In other embodiments, the container 200,201 has markings and/or engravings indicating the length and diameter of the different dental cylindered pins 100 it holds. In certain embodiments, the container 200 has designated cavities or holes 202, each designed to fit a specific dental cylindered pin 100 with a specific diameter and length. In such a case, when the container 200 holds all the dental pins 100, the upper surface of all of said pins 100 is aligned (FIG. 2). In other embodiments, the cavities or holes 203 in the container 201 are identical and designed to fit dental cylindered pins 100 with a specific diameter (FIG. 3). In such a case, when the container 201 holds all the dental cylindered pins 100, the upper surface of all of said pins is not aligned, and each pin protrudes according to its length.

In certain embodiments, the dental kit of the present invention comprises a plurality of dental cylindered pins 100 each independently as defined above, wherein each one of said dental cylindered pins 100 has a particular combination of an outer diameter in a range of about 2.0 mm to about 4.5 mm, and length in a range of about 3.5 mm to about 18 mm.

In certain embodiments, the dental kit of the invention comprises more than one, i.e., two, three, four, five or more, dental cylindered pins 100 having identical diameter and different lengths. Particular such dental kits include one or more, i.e., one, two, three or more, sets of dental cylindered pins 100 having identical diameter and different lengths, wherein each one of said sets consists of two or more, i.e., two, three, four or more, dental cylindered pins 100 having identical diameter and different lengths. In more particular embodiments, the dental kit of the invention comprises at least one set of three or more dental cylindered pins 100 having identical diameter and different lengths.

In certain embodiments, the dental kit of the invention comprises more than one, i.e., two, three, four, five or more, dental cylindered pins 100 having identical lengths and different diameters. Particular such dental kits include one or more, i.e., one, two, three or more, sets of dental cylindered pins 100 having identical length and different diameters, wherein each one of said sets consists of two or more, i.e., two, three, four or more, dental cylindered pins 100 having identical length and different diameters. In more particular embodiments, the dental kit of the invention comprises at least one set of three or more dental cylindered pins 100 having identical length and different diameters.

In certain embodiments, the dental kit of the invention comprises more than one, i.e., two, three, four, five or more, dental cylindered pins 100 having identical length and different diameters; and more than one, i.e., two, three, four, five or more, dental cylindered pins 100 having identical diameter and different lengths. Particular such dental kits include one or more, i.e., one, two, three or more, sets of dental cylindered pins 100 having identical length and different diameters, wherein each one of said sets consists of two or more, i.e., two, three, four or more, dental cylindered pins 100 having identical length and different diameters; and one or more, i.e., one, two, three or more, sets of dental cylindered pins 100 having identical diameter and different lengths, wherein each one of said sets consists of two or more, i.e., two, three, four or more, dental cylindered pins 100 having identical diameter and different lengths. In more particular embodiments, the dental kit of the invention comprises at least one set of three or more dental cylindered pins 100 having identical length and different diameters, as well as at least one set of three or more dental cylindered pins 100 having identical diameter and different lengths.

The insertion/removal apparatus 300 comprised within the dental kit of the present invention is designed for insertion/removal of a dental cylindered pin 100 as defined above into/from an implant socket, by attaching-to and detaching-from said dental cylindered pin 100. Accordingly, in order to insert a dental cylindered pin 100 according to the invention into a drilled dental socket, said pin should first be attached to the tip of an insertion/removal apparatus 300, wherein upon insertion into the dental socket, the insertion/removal apparatus 300 is easily detached, i.e., removed, from the dental pin 100. After removal of excess jaw-bone at the dental socket area, the insertion/removal apparatus 300 is re-attached to the inserted dental pin 100 and the pin is then easily removed out of the dental socket. After use, both the dental pin(s) 100 used as well as the insertion/removal apparatus 300 are cleaned and optionally sterilized for re-use.

In a further aspect, the present invention relates to a method for the safe removal of excess jaw-bone around a drilled implant socket, thereby adapting the depth of said implant socket to the length of a dental implant without the risk of excess removal of jaw-bone or damaging said dental implant, said method comprising the steps of: (i) selecting a suitable dental cylindered pin 100 as defined above according to the diameter of the drilled implant socket and the length of the dental implant for insertion into said implant socket, wherein the length of said dental cylindered pin 100 is identical to the length of the dental implant; (ii) optionally, attaching the selected dental cylindered pin 100 to an insertion/removal apparatus 300; (iii) placing said dental cylindered pin 100 in the drilled implant socket; (iv) performing excess jaw-bone removal around and up to the upper surface of said dental cylindered pin, thereby adapting the depth of the drilled implant socket to the length of the dental implant; (v) attaching said insertion/removal apparatus 300 to the dental cylindered pin 100; and (vi) removing the dental cylindered pin 100 from the depth-adapted implant socket. It should be noted that the diameter of the drilled dental socket may vary and is dependent on the drill used by the dentist/surgeon according to personal preference and/or limitations of the drilling location and bone condition and structure.

It should further be noted that although it would be easier to place the pins 100 of the invention by the aid of the insertion/removal apparatus 300, a skilled dentist/surgeon might be able to place such a pin in a dental implant socket manually, i.e., without the need of the insertion/removal apparatus 300 of the invention.

In certain embodiments, the attachment of said insertion/removal apparatus 300 to the dental cylindered pin 100 of the invention in steps (ii) and (v) of said method is performed by any suitable means, e.g., by a magnet or bulges 305 in said apparatus that interlock into a dedicated lifting groove 105 in the dental cylindered pin 100, or vise-versa, or by screwing 304 (FIG. 4A) said apparatus into a screw-like engraving 104 in said pin.

The method of the present invention enables removing excess jaw bone around a drilled dental implant socket, without the risk of excessive bone removal or damaging the dental implant, by utilizing a dental cylindered pin 100 having selected outer diameter and length, which is inserted into the dental implant socket, optionally by a dedicated insertion/removal apparatus 300, and assists in performing precise removal of the excess jaw-bone around the implant socket prior to the placement of an implant in said implant socket.

Thus, after drilling the dental implant socket, the dentist/ surgeon selects a suitable dental cylindered pin 100 as defined above according to the diameter of the last drill used in drilling the implant socket and the length of the dental implant for placing into the implant socket. The dental cylindered pin 100 may be selected from a plurality of such pins contained within a dental kit as defined above, and is then optionally attached to the insertion/removal apparatus 300 and inserted into the dental implant socket. Once the dental pin 100 is located in the dental socket, the insertion/ removal apparatus 300, if used for insertion of the dental cylindered pin, is detached from the pin, and the dentist/ surgeon may continue performing the excess jaw-bone removal using any of the surgical techniques available. Once the excess jaw-bone around the neck of the dental cylindered pin 100 is removed, the insertion/removal apparatus 300 is attached to the pin and the pin is easily and smoothly removed, i.e., taken out, from the dental implant socket.

After performing the above steps, the jaw-bone level around the dental socket is at the precise depth of the dental implant for placing into the dental socket, and so the dental implant can be screwed into the dental socket until the dental implant's upper surface reaches the crestal bone level of the dental socket.

Unless otherwise indicated, all numbers used in this specification, expressing diameters or lengths of the dental cylindered pins defined above and used according to the method of the present invention, are to be understood as being modified in all instances by the term "about". Accordingly, unless indicated to the contrary, the numerical parameters set forth in this specification are approximations that may vary by up to plus or minus 10% depending upon the desired properties to be obtained by the present invention.

Specific, non-limiting, embodiments of the invention will now be illustrated with reference to the accompanying figures.

FIG. 1 describes four possible examples of the dental cylindered pin 100 according to the invention, from two viewing angles: a side cross section and upper view. FIGS. 1A and 1B show a hollow pin with screw-like engraving 104 all across; FIGS. 1C and 1D show a solid pin; FIGS. 1E and 1F show a pin with screw-like engraving 104 only near the pin's edges; and FIGS. 1G and 1H show a pin with grooves 105 at the pin's edges.

Exemplary configurations of a container 200,201,204 according to the invention are shown in FIGS. 2-4. FIGS. 2A-2C show a specific configuration of the body 200 of the container in which the depth of the cavities 202 for holding the dental cylindered pins 100 of the invention is dependent on the length of the pins themselves, and FIGS. 2D-2F show a corresponding lid 210 thereof. FIGS. 3A-3C show a specific configuration of the body 201 of the container in which the depth of all the cavities 203 for holding the dental cylindered pins 100 are identical, and FIGS. 3D-3F show a corresponding lid 211 thereof, in which the cavities therein are at different heights in order to embrace the protruding pins. In certain embodiments, the lid may be a simple hollow lid, and might not have any cavities therein. FIGS. 4D and 4E show another specific configuration of the body 204 now with a special cavity for an insertion/removal apparatus 300 of the invention. This special cavity is designed according to the insertion/removal apparatus 300 being used.

Figure 1G:
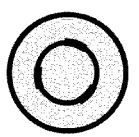
Figure 1H:
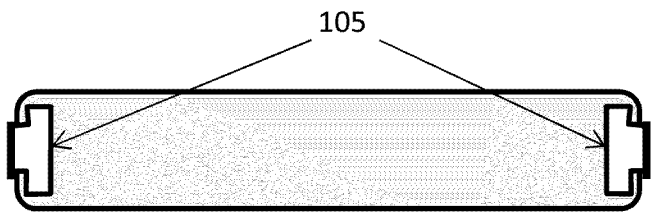

FIGS. 4A-4C demonstrate two exemplary configurations of an insertion/removal apparatus 300 according to the present invention: one with screw-like engravings 304 at its tip (FIG. 4A) suitable for screwing into dental cylindered pins 100 with screw-like engravings therein (FIGS. 1B and 1F), and another with protrusions 305 at its tip (FIGS. 4B and 4C) suitable for interlocking with dental cylindered pins 100 with designated grooves 105 (FIGS. 1G and 1H).

The invention claimed is:

1. A dental kit comprising:
   (i) at least one dental cylindered pin suitable for controlling an amount of jawbone to be removed from a top surface of said jaw-bone after drilling of an implant socket prior to a placement of a dental implant into said drilled implant socket, said dental cylindered pin having an outer diameter in a range of about 2.0 mm to about 4.5 mm and a length in a range of about 3.5 mm to about 18 mm; and
   (ii) an insertion/removal apparatus for inserting/removing said at least one dental cylindered pin into/from the drilled implant socket.

2. The dental kit of claim 1 further comprising a designated container having a body and a lid, for holding said at least one dental cylindered pin and optionally said insertion/ removal apparatus.

3. The dental kit of claim 2, wherein said designated container comprises cavities suited for holding said at least one dental cylindered pin and optionally said insertion/ removal apparatus.

4. The dental kit of claim 1, comprising at least one set of 3 or more dental cylindered pins having identical diameter and different lengths.

5. The dental kit of claim 1, comprising at least one set of 3 or more dental cylindered pins having identical length and different diameters.

6. The dental kit of claim 1, comprising at least one set of 3 or more dental cylindered pins having identical length and different diameters, and at least one set of 3 or more dental cylindered pins having identical diameter and different lengths.

7. The dental kit of claim 1, wherein said insertion/ removal apparatus is designed for insertion/removal of the dental cylindered pin into/from the implant socket by attaching-to and detaching-from said dental cylindered pin.

8. The dental kit of claim 1, wherein said dental cylindered pin is a hollow cylinder, optionally having a screw-like engraving in its inner side, which is optionally engraved either through the entire inner side or only near both edges of the pin.

9. The dental kit of claim 1, wherein said dental cylindered pin has a lifting groove at one or both of its ends.

10. The dental kit of claim 1, wherein said dental cylindered pin is made from medical graded material such as stainless steel or titanium.

11. A method for safe removal of excess jaw-bone around a drilled implant socket after the drilling of the implant socket and prior to the placement of the dental implant into the drilled implant socket, thereby adapting a depth of said implant socket to the length of the dental implant by removing excess jaw-bone from an upper surface of said implant socket, without the risk of excess removal of jaw-bone or damaging said dental implant, said method comprising:

(i) selecting a dental cylindered pin suitable for controlling an amount of the jaw-bone to be removed from a top surface of said jaw-bone after drilling of the implant socket prior to the placement of the dental implant into said drilled implant socket, said dental cylindered pin having an outer diameter in a range of about 2.0 mm to about 4.5 mm and a length in a range of about 3.5 mm to about 18 mm, according to the diameter of the drilled implant socket and the length of the dental implant for insertion into said implant socket, wherein the length of said dental cylindered pin is identical to the length of the dental implant;

(ii) optionally, attaching the selected dental cylindered pin to an insertion/removal apparatus;

(iii) placing said dental cylindered pin in the drilled implant socket;

(iv) removing excess jaw-bone from the top surface of said jaw-bone up to the upper surface of said dental cylindered pin, thereby adapting the depth of the drilled implant socket to the length of the dental implant to be inserted;

(v) attaching said insertion/removal apparatus to the dental cylindered pin; and (vi) removing the dental cylindered pin from the depth-adapted implant socket.

12. The method of claim 11, wherein the dental cylindered pin is attached to the insertion/removal apparatus by a magnet or bulges in the insertion/removal apparatus interlocking into a lifting groove in the dental cylindered pin, or by screwing the insertion/removal apparatus into the dental cylindered pin.

* * * * *